(12) United States Patent
Hafezi et al.

(10) Patent No.: US 9,052,448 B2
(45) Date of Patent: Jun. 9, 2015

(54) TWO-DIMENSIONAL COUPLED RESONATOR OPTICAL WAVEGUIDE ARRANGEMENTS AND SYSTEMS, DEVICES, AND METHODS THEREOF

(75) Inventors: Mohammad Hafezi, Washington, DC (US); Jacob Taylor, Washington, DC (US); Eugene Demler, Newton, MA (US); Mikhail Lukin, Cambridge, MA (US)

(73) Assignees: University of Maryland, College Park, College Park, MD (US); President and Fellows of Harvard College, Cambridge, MA (US); The United States of America, as represented by the Secretary of Commerce, Washington, DC (US)

( * ) Notice: Subject to any disclaimer, the term of this patent is extended or adjusted under 35 U.S.C. 154(b) by 411 days.

(21) Appl. No.: 13/366,122

(22) Filed: Feb. 3, 2012

(65) Prior Publication Data

US 2012/0308181 A1 Dec. 6, 2012

Related U.S. Application Data

(60) Provisional application No. 61/439,053, filed on Feb. 3, 2011.

(51) Int. Cl.
*G02B 6/42* (2006.01)
*G02B 6/00* (2006.01)
(Continued)

(52) U.S. Cl.
CPC .......... *G02B 6/12007* (2013.01); *G01N 21/552* (2013.01); *G01N 21/41* (2013.01); *G02B 6/12* (2013.01); *H04J 14/02* (2013.01); *G02B 6/29331* (2013.01); *H04J 14/00* (2013.01)

(58) Field of Classification Search
CPC ........ G02B 6/12; G02B 6/12007; G02B 6/28; G02B 6/29331; G01N 21/41; G01N 21/552; G01N 21/8477; H04J 14/00; H04J 14/02
USPC .......... 385/1, 3, 6, 12, 16, 27, 28, 30, 31, 32, 385/39, 43, 50, 129–132; 435/287.1; 422/82.05; 356/128; 398/43, 45, 53, 398/79, 82, 87
See application file for complete search history.

(56) References Cited

U.S. PATENT DOCUMENTS 6,897,434 B1 * 5/2005 Kumar et al. ............ 250/227.18
2005/0053375 A1 * 3/2005 Yoo et al. ........................ 398/53
(Continued)

OTHER PUBLICATIONS

Yariv et al., "Coupled-resonator optical waveguide: a proposal and analysis," Optics Letters, Jun. 1, 1999, vol. 24 No. 11, pp. 711-713.
(Continued)

*Primary Examiner* — Akm Enayet Ullah
*Assistant Examiner* — Michael Mooney
(74) *Attorney, Agent, or Firm* — Miles & Stockbridge P.C.; Frederick F. Rosenberger; Otilia Gabor

(57) ABSTRACT

Two-dimensional coupled resonator optical waveguide arrangements and systems, devices, and methods thereof. Networks of coupled resonator optical waveguides are arranged so as to exploit topological properties of these optical networks. Such arrangement affords topological protection against disorders or perturbations in the network that may hinder or block photon flow. As a result of a disorder, photons traversing along edge states of the array are rerouted based on the disorder or perturbation. Photon routing in the network is accordingly protected against disorder or defects.

22 Claims, 10 Drawing Sheets

(51) Int. Cl.
| | |
|---|---|
| C12M 1/34 | (2006.01) |
| G01N 21/00 | (2006.01) |
| G01N 21/41 | (2006.01) |
| H04J 14/02 | (2006.01) |
| G02B 6/12 | (2006.01) |
| G01N 21/552 | (2014.01) |
| G02B 6/293 | (2006.01) |
| H04J 14/00 | (2006.01) |

(56) References Cited

U.S. PATENT DOCUMENTS

2005/0169582 A1* 8/2005 Tan et al. .................... 385/50
2006/0239614 A1* 10/2006 Montgomery et al. ......... 385/39
2007/0269901 A1 11/2007 Armani et al.

OTHER PUBLICATIONS

De Vos et al., "Optical Biosensor based on Silicon-on-Insulator Microring Cavities for Specific Protein Binding Detection," Nanoscale Imaging, Spectroscopy, Sensing, and Actuation for Biomedical Applications IV, Proceedings of SPIE, vol. 6447, pp. 64470K-1 to 64470K-8.
Iqbal et al., "Label-Free Biosensor Arrays Based on Silicon Ring Resonators and High-Speed Optical Scanning Instrumentation," IEEE Journal of Selected Topics in Quantum Electronics, vol. 16, No. 3, May/Jun. 2010, pp. 664-61.
Claes et al., "Label-Free Biosensing With a Slot-Waveguide-Based Ring Resonator in Silicon on Insulator," IEEE Photonics Journal, vol. 1, No. 3, Sep. 2009, pp. 197-204.
Fan et al., "Overview of Novel Integrated Optical Ring Resonator Bio/Chemical Sensors."
Flueckiger et al., "Label-Free Biosensing Using Cascaded Silicon-on-Insulator Micro-racetrack Resonators Integrated with PDMS Microfluidic Channels," 15th International Conference on Miniaturized Systems for Chemistry and Life Sciences, Oct. 2-6, 2011, pp. 565-567.
Hao Li & Xudong Fan, "Characterization of Sensing Capability of Optofluidic Ring Resonator Biosensors," Applied Physics Letters 97, 011105 (2010), pp. 011005-1 to 01105-3.
Scheuer et al., "Coupled Resonator Optical Waveguides (CROWs)."
Harada et al., "Indistinguishable Photon Pair Generation Using Two Independent Silicon Wire Waveguides," New Journal of Physics 13 (2011) 065005, pp. 1-12.
Joyce Kai See Poon, "Active and Passive Coupled-Resonator Optical Waveguides," California Institute of Technology, Pasadena CA, Defended May 21, 2007.
International Search Report dated Jun. 19, 2012 for International Application No. PCT/US12/23847.
Written Opinion dated Jun. 19, 2012 for International Application No. PCT/US12/23847.
Almeida et al., "All-optical control of light on a silicon chip," Nature, Oct. 2004, 431(28): pp. 1081-1084.
Anderson, P.W. "Absence of Diffusion in Certain Random Lattices," Physical Review, Mar. 1958, 109(5): pp. 1492-1505.
Baba, T. "Slow light in photonic crystals," Nature Photonics, Aug. 2008, 2: pp. 465-473.
Barwicz et al., "Fabrication of Add-Drop Filters Based on Frequency-Matched Microring Resonators," IEEE Journal of Lightwave Technology, May 2006, 24(5): pp. 2207-2218.
Bernevig et al., "Quantum Spin Hall Effect," Physical Review Letters, Mar. 2006, 96(10):106802.
Borselli et al., "Beyond the Rayleigh scattering limit in high-Q silicon microdisks: theory and experiment", Optics Express, Mar. 2005, 13(5): pp. 1515-1530.
Bychkov et al., "Oscillatory effects and the magnetic susceptibility of carriers in inversion layers," Journal of Physics C: Solid State Physics, 1984, 17: pp. 6039-6045.
Cho et al., "Fractional Quantum Hall State in Coupled Cavities," Physical Review Letters, Dec. 2008, 101(24):246809.

Cooper, N.R. "Rapidly rotating atomic gases" Advances in Physics, 2008, 57(6): pp. 539-616.
Fan et al., "Theoretical analysis of channel drop tunneling processes," Physical Review B, Jun. 1999, 59(24): pp. 882-892.
Gardiner et al., "Input and output in damped quantum systems: Quantum stochastic differential equations and the master equation," Physical Review A, Jun. 1985, 31(6): pp. 3761-3774.
Hafezi et al., "Photonic quantum transport in a nonlinear optical fiber," Nov. 2009, arXiv:0907.5206v2, [quant-ph].
Haldane et al., "Possible Realixation of Directional Optical Waveguides in Photonc Crystals with Broken Time-Reversal Symmetry," Physical Review Letters, Jan. 2008, 100(1):013904.
Haldane, F.D.M., "Model for a Quantum Hall Effect without Landau levels: Condensed-Matter Realization of the 'Parity Anomaly'," Physical Review Letters, Oct. 1988, 61(18): pp. 2015-2018.
Halperin, B.I., "Quantized Hall conductance, current-carrying edge states, and the existence of extended states in a two-dimensional disordered potential," Physical Review B, Feb. 1982, 25(4):pp. 2185-2190.
Hatsugai, Y., "Edge states in the integer quantum Hall effect and the Riemann surface of the Bloch function," Physical Review B, Oct. 1993, 48(16): pp. 11851-11862.
Heebner et al., "Enhanced linear and nonlinear optical phase response of AlGaAs microring resonators," Optics Letters, Apr. 2004, 29(7): pp. 769-771.
Hofstadter, D.R., "Energy levels and wave functions of Bloch electrons in rational and irrational magnetic fields," Physical Review B, Sep. 1976, 14(6): pp. 2239-2249.
Huckestein, B., "Scaling theory of the integer quantum Hall effect", Review of Modern Physics, Apr. 1995, 67(2): pp. 357-396.
Jeckelmann et al., "The quantum Hall effect as an electrical resistance standard," Reports on Progress in Physics, Nov. 2001, 64: pp. 1603-1655.
Kane et al., "Quantum Spin Hall Effect in Graphene," Physical Review Letters, Nov. 2005, 95(22):226801.
Kippenberg et al., "Modal coupling in traveling-wave resonators," Optics Letters, Oct. 2002, 27(19):pp. 1669-1671.
Kitaev, A.Y., "Fault-tolerant quantum computation by anyons," Annals of Physics, May 2002, 303: pp. 2-30.
Kitagawa et al., "Exploring topological phases with quantum walks," Physical Review A, Sep. 2010, 82(3): 033429.
Klitzing, K.V., "New Method for High-Accuracy Determination of the Fine-Structure Constant Based on Quantized Hall Resistance", Physical Review Letters, Aug. 1980, 45(6): pp. 494-497.
Koch et al., "Time-reversal-symmetry breaking in circuit-QED-based photon lattices," Physical Review A, Oct. 2010, 82(4): 043811.
Konig et al., "Quantum Spin Hall Insulator State in HgTe Quantum Wells," Science, Nov. 2007, 318: pp. 766-770.
Kramer et al., "Localization: theory and experiment," Reports on Progress in Physics, 1993, 56: pp. 1469-1564.
Langbein, D., "The Tight-Binding and the Nearly-Free-Electron Approach to Lattice Electrons in External Magnetic Fields," Physical Review, Apr. 1969, 180(3): pp. 633-648.
Liang et al., "Transmission characteristics of a Fabry-Perot etalon-microtoroid resonator coupled system," Optics Letters, Feb. 2006, 31(4): pp. 510-512.
Mookherjea et al., "Localization in silicon nanophotonic slow-light waveguides," Nature Photonics, Feb. 2008, 2: p. 90-93.
Nayak et al., "Non-Abelian Anyons and Topological Quantum Computation," Mar. 2008, arXiv:0707.1889v2 [cond-mat.str-el]: pp. 1-73.
Novoselov et al., "Room-Temperature Quantum Hall Effect in Graphene," Science, Mar. 2007, 315: p. 1379.
Otterbach et al., "Effective Magnetic Fields for Stationary Light," Physical Review Letters, Jan. 2010, 104(3): 033903.
Poon et al., "Transmission and group delay of microring coupled-resonator optical waveguides," Optics Letters, Feb. 2006, 31(4): pp. 456-458.
Poon, J.K.S., "Designing coupled-resonator optical waveguide delay lines," Journal of the Optical Society of America B, Sep. 2004, 21(9): pp. 1665-1673.

(56) References Cited

OTHER PUBLICATIONS

Rammal et al., "Quantized Hall conductance and edge states: Two-dimensional strips with a periodic potential," *Physical Review B*, Apr. 1983, 27(8): pp. 5142-5145.

Thouless et al., "Quantized Hall Conductance in a Two-Dimensional Periodic Potential," *Physical Review Letters*, Aug. 1982, 49(6): pp. 405-408.

Tsui et al., "Two-Dimensional Magnetotransport in the Extreme Quantum Limit," *Physical Review Letters*, May 1982, 48(22): pp. 1559-1562.

Wang et al., "Observation of unidirectional backscattering-immune topological electromagnetic states," *Nature*, Oct. 2009, 461: pp. 772-776.

Wang et al., "Reflection-Free One-Way Edge Modes in a Gyromagnetic Photonic Crystal," *Physical Review Letters*, Jan. 2008, 100(1): 013905.

Xia et al., "Coupled resonator optical waveguides based on silicon-on-insulator photonic wires," *Applied Physics Letters*, 2006, 89(4): 041122.

Xia et al., "Mode conversion losses in silicon-on-insulator photonic wire based racetrack resonators," *Optics Express*, May 2006, 14(9): pp. 3872-3886.

Xia et al., "Ultracompact optical buffers on a silicon chip," *Nature Photonics*, Jan. 2007, 1: pp. 65-71.

Xu et al., "Scattering-theory analysis of waveguide-resonator coupling," *Physical Review E*, Nov. 2000, 62(5): pp. 7389-7404.

\* cited by examiner

US 9,052,448 B2

TWO-DIMENSIONAL COUPLED RESONATOR OPTICAL WAVEGUIDE ARRANGEMENTS AND SYSTEMS, DEVICES, AND METHODS THEREOF

CROSS-REFERENCE TO RELATED APPLICATIONS

This application claims priority to and the benefit of U.S. Provisional Application No. 61/439,053 filed Feb. 3, 2011, the content of which is incorporated herein by reference in its entirety.

FEDERALLY SPONSORED RESEARCH AND DEVELOPMENT STATEMENT

This invention was made with government support under Grant/Contract No. W911NF0910406 awarded by the Army Research Office ("ARO"). The government has certain rights in the invention.

FIELD

The present invention relates to a two-dimensional array or lattice of coupled resonators that form an optical waveguide. In particular, embodiments of the present invention involve a network of coupled resonator optical waveguides (CROWs) in two dimensions.

Two-dimensional networks of coupled resonator optical waveguides according to embodiments of the present invention can be implemented in, inter alfa, optical processing circuitry (optical logic, delay lines, data storage, parallel processing, etc.), mechanical sensors, photon pair generation devices or systems, and sensors or sensing systems, such as biosensors or biosensing systems.

BACKGROUND

Generally speaking, any one-dimensional resonator optical waveguide is not robust or robust enough against disorders or perturbations caused by defects in its corresponding wafer, defects due to fabrication errors, and/or defects due to degradation over time. In the case of fabrication errors, such errors can include irregularities in the fabrication of the resonators, for instance, resulting in resonators in the row with non-uniform dimensions. Such defects can be problematic in that they can deflect or degrade the quality of light passing through the waveguide. Consequentially, the light output signal can have unwanted modulation in the output signal (i.e., noise) at best and can be undetectable in a worst-case scenario, thereby reducing or blocking transmission of information.

In the case of resonators in the form of silicon-, sapphire-, GaAr-, or silicon-insulator-based micro-rings, for instance, fabrication errors can cause a change in width, length, height, and/or surface roughness, which can lead to resonance mismatch between adjacent resonator micro-rings. An example of a situation where a defect may occur over time is where the chip in which the waveguide resides is subjected to a temperature gradient for a prolonged period of time (i.e., one portion of the chip has a temperature different from another portion). Impurities in the substance (e.g., silicon) in which the resonators are formed can also lead to disorders or perturbations.

In the case of a one-dimensional coupled resonator optical waveguide (CROW) used as a photon delay device, any of the aforementioned defects can be particularly problematic. One-dimensional photonic delay devices can be constructed from a single row of resonators, such as micro-rings or micro-racetracks. A defect in any one resonator, any waveguide between the resonators, or an accumulation of defects along the row of resonators can degrade or block transmission of photons through the waveguide. For instance, the length of delay for a delay device can be given by the size of the array or the length of the photon's path. As the number of resonators and optical features is increased to accommodate longer delays, inherent defects along the photon path can eventually cause a roadblock for the photons. As an example, for a fixed disorder strength (e.g., a fixed disorder), the waveguide may be operational (i.e., allow sufficient passage of photons) with ten (10) series-connected resonators, but may not be operational with one hundred (100) series-connected resonators. The shorter transmission path may have noise, but the longer transmission path is blocked.

FIG. 1 is an illustration of a one-dimensional array 100 of coupled resonators. The array can be used as a waveguide in an optical delay circuit.

The one-dimensional array 100 can include a plurality of resonators, micro-rings 106 in this case, that are serially arranged on a substrate 102. Though FIG. 1 shows seven (7) micro-rings, any suitable number of micro-rings may be implemented, of course, taking into consideration losses and accumulating defects.

Generally speaking, the micro-rings 106 may be formed in a surface of the substrate 102 and can be overlain with a cladding (not explicitly shown). A light source 104 to the array is arranged adjacent a micro-ring 106 at one end of the array. The light source to the array can be a waveguide (e.g., a thin ridge formed in a silicon surface), in which light signals can propagate from a light generation means, such as a laser or light-emitting diode (LED). Light can travel through the light source 104 and can be evanescently side-coupled to the first micro-ring 106 in the array depending upon the frequency of the light signals and the corresponding structure of the first micro-ring 106 in the array. The light signals can be propagated through the micro-rings 106 in the array through direct coupling of adjacent micro-rings 106 as shown by the arrows in FIG. 1, in alternating fashion. The light signals may be delayed as they travel around the micro-rings and from micro-ring to micro-ring. The light signals may be returned to light source 104 and output, or they may be output (via evanescent coupling) at the other side of the array via a light outputting means, such as a waveguide 105.

SUMMARY

The Summary describes and identifies features of some embodiments. It is presented as a convenient summary of some embodiments, but not all. Further the Summary does not necessarily identify critical or essential features of the embodiments, disclosed subject matter, or claims.

The present invention involves a network of coupled resonator optical waveguides (CROWs) in two dimensions. Networks of coupled resonator optical waveguides according to embodiments of the present invention can each be arranged so as to exploit topological properties of these optical networks. Such arrangement can afford topological protection against defects or disorders in the network that may hinder or block photon flow, thereby providing a means by which the photons may be routed (rerouted) based on the defect or disorder. Thus, photon routing in the network can protect against disorder or defects to provide a robust optical network.

Embodiments of the present invention can comprise (i.e., include), a topologically protected silicon optical delay line which includes: a two-dimensional array of coupled micro-resonator optical waveguides having four or more micro-resonators, said two-dimensional array being of any geometry; an input waveguide arranged adjacent to a first micro-resonator of the four or more micro-resonators such that light signals in said input waveguide are coupled to only said first micro-resonator and not any other micro-resonators of said four or more micro-resonators; and an output waveguide arranged adjacent to a second micro-resonator of said four or more micro-resonators, different from said first micro-resonator, such that light signals are coupled from only said second micro-resonator to said output waveguide and not from any other micro-resonators of said four or more micro-resonators. Optionally, the input waveguide may be evanescently coupled to the first micro-resonator. Additionally or optionally, the output waveguide may be evanescently coupled to the second micro-resonator. Further, the two-dimensional array is arranged so as to be operative to provide topological protection against any disorders in said two-dimensional array, the topological protection including providing an alternative pathway for light signals traveling along a portion of the perimeter of said two-dimensional array based on photonic edge states thereof such that the light signals bypass any disorder in a light signal path from said first micro-resonator to said second micro-resonator. Optionally, the disorder may be located at the perimeter of the two-dimensional array.

Optionally, the portion of the perimeter for the light signal path from said first micro-resonator to said second micro-resonator is less than the entire perimeter of said two-dimensional array. Edge state transmission along the portion of the perimeter for said two-dimensional array is based on the operational bandwidth of said four or more micro-resonators in said two-dimensional array. The light signals traveling along the portion of the perimeter of said two-dimensional array based on photonic edge states thereof do so based on a magnetic field. Optionally, the magnetic field is a perpendicular artificial or pseudo magnetic field. The magnetic field is optionally a non-externally applied magnetic field. In embodiments, the magnetic field is an effective magnetic field generated based on phase tuning of waveguides connecting said four or more micro-resonators, said phase tuning being based on the respective lengths of the connecting waveguides and/or a change in an index of refraction for the connecting waveguides. Optionally, the delay line is a variable delay line, the variability of the delay being based on at least one of a switch or switches coupling or decoupling said two-dimensional array in series with one or more other one- or two-dimensional arrays, changing the index of refraction for said two-dimensional array, a PIN junction, a heating element providing a uniform heat distribution, and a metal-oxide-semiconductor capacitor structure. In embodiments, the four or more micro-resonators of said two-dimensional array are arranged as a square, a rectangle, a disk, an oval, a diamond, a triangle, or any other shape having the same topology of these arrangements. Optionally, the delay line is provided in an optical computation and communication system.

Embodiments also include a fault-tolerant optical system comprising: a two-dimensional waveguide array of coupled optical resonators, said two-dimensional array being of any geometry; one or more input waveguides operatively coupled to said two-dimensional waveguide array; and one or more output waveguides operatively coupled to said two-dimensional waveguide array. Faults for which the system is tolerant include faults caused by one or more of defects in a corresponding wafer, defects due to fabrication errors, and defects due to degradation over time.

Optionally, the system can further comprise: a light transmitter to transmit light signals to said two-dimensional waveguide array via said one or more input waveguides; a light receiver to receive light signals from said two-dimensional waveguide array via said one or more output waveguides; and a processor to receive and process data from said light receiver based on the received light signals. The system can be a delay system in a computer system or a communication system, a sensing system, or a system for generating photon pairs. Optionally, the two-dimensional waveguide array of coupled optical resonators are operatively multiplexed with a plurality of other said two-dimensional waveguide arrays of coupled optical resonators.

Additionally included in embodiments is a method for routing photons comprising: receiving a photon at an access portion of a topologically protected two-dimensional lattice of coupled resonators; and outputting the photon from the topologically protected two-dimensional lattice of coupled resonators at an egress portion thereof. The outputting the photon is after the photon has traversed a path of edge states of the topologically protected two-dimensional lattice of coupled resonators in accordance with an effective magnetic field associated with the edge states.

The method can optionally further comprise applying a solution to a surface associated with the topologically protected two-dimensional lattice of coupled resonators; and sensing a molecule-molecule interaction at the interface of the surface and the solution. Alternatively, the method can further comprise outputting a photon pair based on said outputting the photon from the topologically protected two-dimensional lattice of coupled resonators. Optionally, the method can include dynamically varying the time it takes the photon to be outputted by said outputting from the time of said receiving.

Embodiments of the present invention include a topologically protected silicon on insulator (SOI) optical delay line comprising: a two-dimensional array of coupled micro-ring resonator optical waveguides, said two-dimensional array being arranged in plan view as an N×M rectangular lattice of the micro-ring resonators, where N and M are both positive integers greater than two; an input waveguide arranged adjacent only to a first micro-ring resonator of the plurality of micro-ring resonators such that light signals of a select frequency band travelling in said input waveguide are evanescently coupled to said first micro-ring resonator; and an output waveguide arranged adjacent to only a second micro-ring resonator of the plurality of micro-ring resonators, different from said first micro-ring resonator, such that light signals are evanescently coupled from said second micro-ring resonator to said output waveguide. The two-dimensional array can be arranged so as to be operative to provide topological protection against any disorders in the two-dimensional array, the topological protection including providing an alternative pathway for the light signals travelling along the edge states of said two-dimensional array such that they bypass any disorders at the edge of said two dimensional array.

Optionally, N and M are equal. Further, edge state paths for said two-dimensional array are different based on the frequency of the input light signal, and the frequency for edge state transmission is set based on the effective magnetic field ($\alpha$) and the decay rate ($\kappa$) of the micro-ring resonators in said two-dimensional array.

Optionally, the delay line is a variable delay line, the variability of the delay being based on at least one of the frequency of the input light signal, a switch or switches coupling or decoupling said two-dimensional array in series with one or more other one- or two-dimensional arrays, changing the index of refraction for said two-dimensional array, a PIN junction, and a heating element providing a uniform heat distribution.

The delay line can reside in a microchip with a computer, or it can be provided in a light signal path of a photon pair generation system.

Embodiments of the present invention also can include a fault-tolerant optical system comprising: a two-dimensional waveguide array of coupled optical resonators; one or more input waveguides operatively coupled to said two-dimensional waveguide array; one or more output waveguides operatively coupled to said two-dimensional waveguide array; a light transmitter to transmit light signals to said two-dimensional waveguide array via said one or more input waveguides; a light receiver to receive light signals from said two-dimensional waveguide array via said one or more output waveguides; and a processor to receive and process data from said light receiver based on the received light signals.

The fault tolerant system can be a system for generating photons pairs, a biosensing system, or a computer system, wherein the two-dimensional waveguide array of coupled optical resonators is operative as a delay device to delay photons input thereto for data storage and retrieval, for instance.

Optionally, in the case of a biosensing system, the two-dimensional waveguide array of coupled optical resonators can be formed in a substrate having an upper cladding covering the resonators, wherein the upper cladding has formed thereon a biolayer formed by chemical treatment, the biolayer facilitating specific molecule-molecule interactions, and wherein a solution containing analytes can be applied to the biolayer, light signals within said two-dimensional waveguide array of coupled optical resonators being responsive to the molecule-molecule interactions, whereby characteristics of the light signals output from said two-dimensional waveguide array of coupled optical resonators are received by said light receiver and processed by said processor in order to determine a characteristic of the molecule-molecule interactions.

Optionally, the two-dimensional waveguide array of coupled optical resonators are operatively multiplexed with a plurality of other said two-dimensional waveguide arrays of coupled optical resonators. Additionally, the biosensing system optionally can be a self-contained system (i.e., a device) that is configured and operative to be disposable and for one-time use only, for example.

The present invention can also include embodiments for a method for routing photons comprising: receiving a photon at an access portion of a topologically protected two-dimensional lattice of coupled resonators; and outputting the photon from the topologically protected two-dimensional lattice of coupled resonators at an egress portion thereof. The outputting the photon is after the photon has traversed a first path about the topologically protected two-dimensional lattice of coupled resonators when the photon does not encounter a specified disorder, the first path being a path around only the perimeter of the lattice, and the outputting the photon is after the photon has traversed a second path about the topologically protected two-dimensional lattice of coupled resonators when the photon encounters the specified disorder.

The method can further comprise applying a solution to a surface associated with the topologically protected two-dimensional lattice of coupled resonators; and sensing a molecule-molecule interaction at the interface of the surface and the solution. Or the method can further comprise outputting a photon pair based on said outputting the photon from the topologically protected two-dimensional lattice of coupled resonators. Methods according to embodiments of the present invention can comprise before said receiving the photon, forming the topologically protected two-dimensional lattice of coupled resonators. Methods can also optionally comprise dynamically varying the time it takes the photon to be outputted by said outputting from the time of said receiving.

For methods according to embodiments of the present invention the resonators of the lattice can be arranged so as to form in plan view one of a square, a rectangle, a disk, an oval, a diamond, a ring, or a triangle.

Embodiments of the present invention can also include a method of providing a topologically protected two-dimensional lattice using an effective magnetic field, the method comprising: receiving a photon at an access portion of the topologically protected two-dimensional lattice; and generating an effective magnetic field based on the received photon. The magnetic field can determine movement of the photon in the topologically protected two-dimensional lattice.

Methods according to embodiments of the present invention also can comprise a method of generating an effective magnetic field based on an arrangement and connections of a two-dimensional lattice, wherein the method comprises: receiving a photon at an access portion of the two-dimensional lattice; and generating an effective magnetic field responsive to the received photon. The magnetic field can determine movement of the photon in the topologically protected two-dimensional lattice.

Additional methods according to embodiments of the present invention can include a method for routing photons comprising: receiving a photon at an access portion of a topologically protected two-dimensional lattice of coupled resonators; and outputting the photon from the topologically protected two-dimensional lattice of coupled resonators at an egress portion thereof. The outputting the photon can be after the photon has traversed a path of edge states of the topologically protected two-dimensional lattice of coupled resonators in accordance with the edge states.

Embodiments of the present invention also can include methods, systems, devices, apparatuses, and computer program products, as shown and described herein.

BRIEF DESCRIPTION OF THE DRAWINGS

The accompanying drawings illustrate embodiments of the disclosed subject matter. The disclosed subject matter will be best understood by reading the ensuing specification in conjunction with the drawing figures, in which like elements are designated by like reference numerals.

DETAILED DESCRIPTION

As discussed above, one-dimensional arrays of resonators can be subject to defects that can negatively impact light signals traversing through the array of resonators. Of course, two-dimensional coupled resonator arrays, to which the present invention is directed, can also be susceptible to such defects. Unlike one-dimensional arrays, however, embodiments of the present invention provide a fault-tolerant network with an alternative pathway for light signals to travel through the array (or a portion of the array) such that they bypass a defect or defects and such that the light signals are protected from disorder or disturbance caused by the defect or defects. Put another way, embodiments of the present invention provide topological protection for the routing of photons, whereby the photons are routed or rerouted such that they are protected against a disorder or a certain amount of disorder.

Two-dimensional resonator arrays according to embodiments of the present invention can be implemented in photon- or electron-based semiconductor chips, such as microchips, whereby one or more two-dimensional arrays can be used as part of optical or photonic processing circuitry, including linear and non-linear active and passive components (e.g., a transistor). As will be discussed in more detail below, applications for the two-dimensional resonator array according to embodiments of the present invention can include optical or photonic processing circuitry, such as photon delay lines, data storage, parallel processing, implemented in a computer (e.g., partial or full quantum computer) or a communication system for instance, as well as photon pair generation devices or systems, and biosensors or biosensing systems. Further, embodiments of the present invention can be employed and operated at room temperature, for example, and do not require any external magnetic field or the use of magnetic materials.

Figure 1:
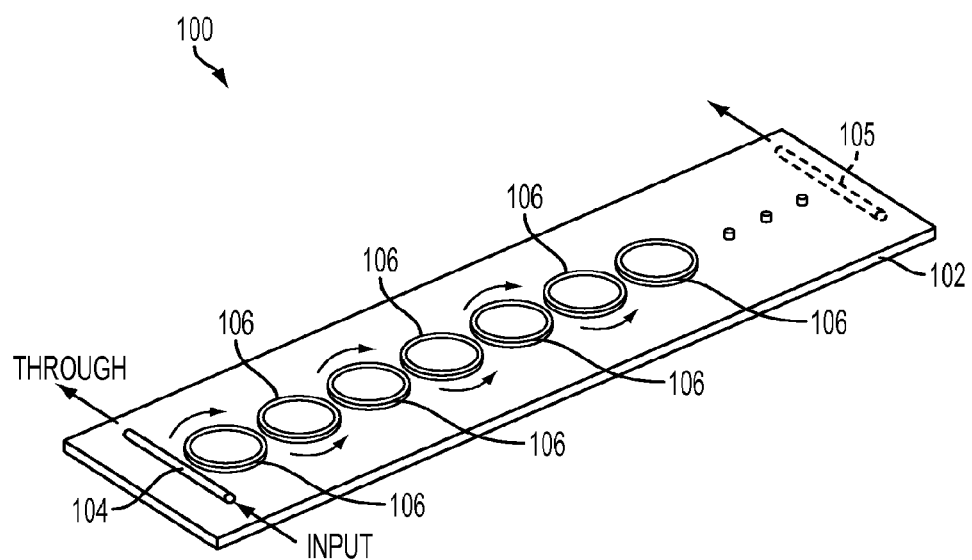
FIG. 1 is an illustration of a one-dimensional array of coupled resonators.
Figure 2A:
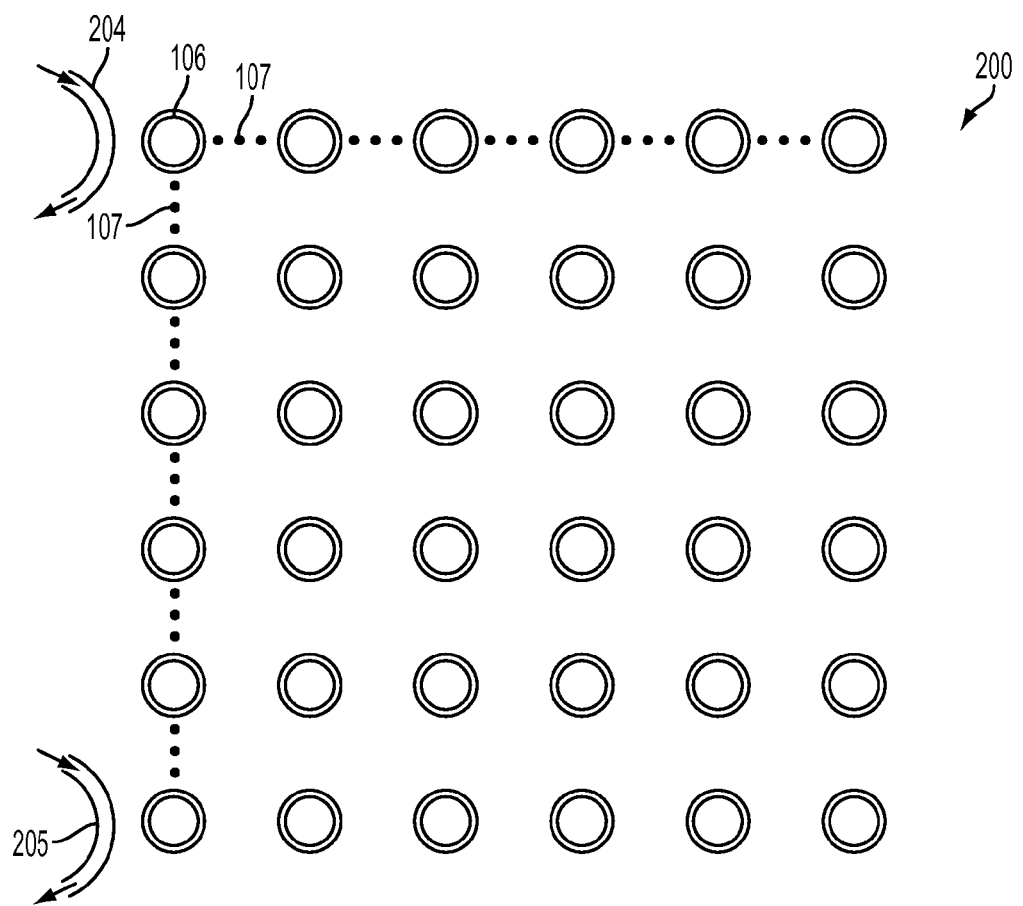
FIG. 2A shows a plan view array of resonators according to embodiments of the present invention.
Figure 2B:
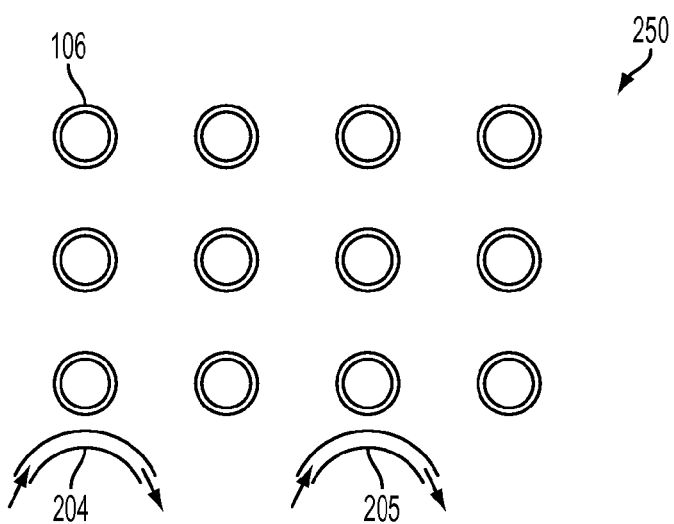
FIG. 2B shows a plan view array of resonators according to other embodiments of the present invention.

FIGS. 2A and 2B are plan view representations of two different examples of two-dimensional arrays of coupled resonator waveguides according to embodiments of the present invention. In FIG. 2A, a 6×6 array 200 of coupled resonators 106 is shown, and in FIG. 2B a 4×3 array 250 of coupled resonators 106 is shown. Essentially, the two-dimensional arrays 200, 250 shown in FIGS. 2A and 2B, respectively, are each comprised of a network of coupled resonator optical waveguides (CROWs). Note that though square and rectangular arrangements are shown, embodiments of the present invention are not limited to these arrangements. For instance, the coupled resonators may be arranged in an array in the form of a disk, an oval, a diamond, a triangle, a honeycomb, an annulus, a ring, etc. Further, optionally, the array may be of any geometry, for instance, tilted or wavy.

In the case of a rectangular configuration, the array may be an N×2 array (or a 2×N), where N is a positive integer greater than one. Further, in embodiments, at least three or at least four coupled resonators may be employed. In the case of only three resonators, each resonator may have its own adjacent waveguide to input or output light signals. In the case of square configurations, embodiments can include 10×10 arrays or 20×20 arrays, for instance. Generally speaking, the arrays can be of any suitable number of coupled resonators, limited by the amount of loss in the resonators, interior or exterior waveguides; the strength of the light applied or to be applied to the array; and/or an amount of a defect, such as a total cumulative impurity amount through the waveguide formed by the array or total inherent defects through the waveguide formed by the array.

The resonators 106 can be any suitable resonators, including micro- or nano-resonators, such as micro- or nano-ring resonators (e.g., planar configurations, dual concentric ring configurations, racetrack configurations, micro-toroid, oval, disk, doughnut, etc.). An input waveguide 205 can be provided adjacent to one of the resonators 106 such that a light signal provided in the waveguide and at a select frequency band can be coupled to the one resonator, thereby gaining access to the array. In embodiments, the input waveguide may also be a resonator, for instance, from a standard one-dimensional CROW. An output waveguide 205 also can be provided, to output light signals from the array after the light signals have traversed a path in the array. Alternatively, the waveguides operation of the waveguides may be switched, with waveguide 205 being to input light signals and waveguide 204 being to output waveguide signals. Optionally, in two-dimensional coupled arrays according to embodiments of the disclosed subject matter, all of the resonators may be substantially the same (i.e., the same type). Alternatively, some or all of the coupled resonators may be different types. In embodiments, an input waveguide may be coupled to multiple resonators. Optionally, the multiple resonators may be adjacent or non-adjacent. Likewise, embodiments may optionally or alternatively have output waveguides coupled to multiple resonators. Optionally these resonators also may be adjacent or non-adjacent.

FIG. 2A has three dots representing "waveguides" 107 between adjacent resonators 106 on two edges of the array. Note that the waveguides 107 between the other resonators 106, both along the other two edges and internally have been intentionally omitted in this figure. FIG. 2B intentionally omits the waveguides 107.

Figure 3A:
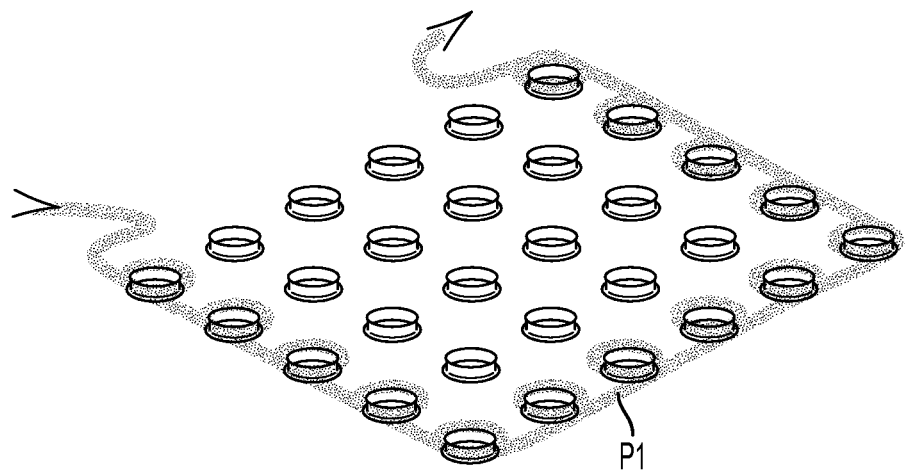
FIGS. 3A and 3B illustrate conceptual operational aspects of the present invention, with FIG. 3A showing an example of edge-state travel of a light signal in an array of resonators without a defect or disturbance, and with FIG. 3B showing an example of edge-state travel of a light signal in the array of resonators with a defect or disturbance.
Figure 3B:
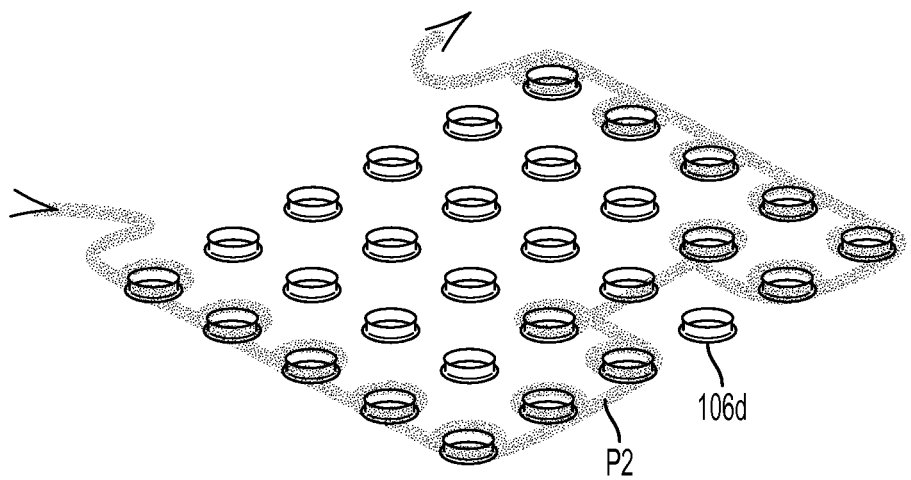

FIGS. 3A and 3B illustrate conceptual operational aspects of the present invention. FIG. 3A shows a conceptual example of an edge-state travel path P1 of a supplied light signal in an array of resonators without a defect or disturbance sufficient to cause rerouting of the light signal. FIG. 3B shows a conceptual example of edge-state travel path P2 of a supplied light signal in the array of resonators with a defect or disturbance at resonator 106d. In FIGS. 3A and 3B the resonators are shown as micro-toroids, but other types of resonators as discussed herein may be implemented.

Discussing further the operation of the two-dimensional array of coupled resonators with respect to FIGS. 3A and 3B, photons are allowed to travel in a path P1 via resonators and corresponding waveguides along the edges of the array, but do not travel to internally arranged resonators, unless they encounters a disorder. The resonators and waveguides of the array can be configured such that only light signals at a certain frequency may enter the array (i.e., coupled). When the light signals are provided to the array at a frequency within an edge state band of the array, the light signals can be caused to travel around the perimeter or edge of the array. In the case of a light signal provided at a frequency in the magnetic band of the array, the photons can travel inside the bulk to one or more internally located resonators. The frequencies can be set or otherwise determined based on the effective magnetic field ($\alpha$) and the decay rate ($\kappa$) of the resonators corresponding waveguides.

Figure 4A:
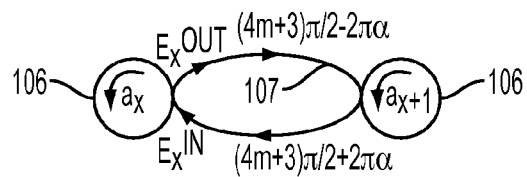
FIGS. 4A-4C are schematics of a photonic system with a synthetic magnetic field according to embodiments of the present invention.
Figure 4B:
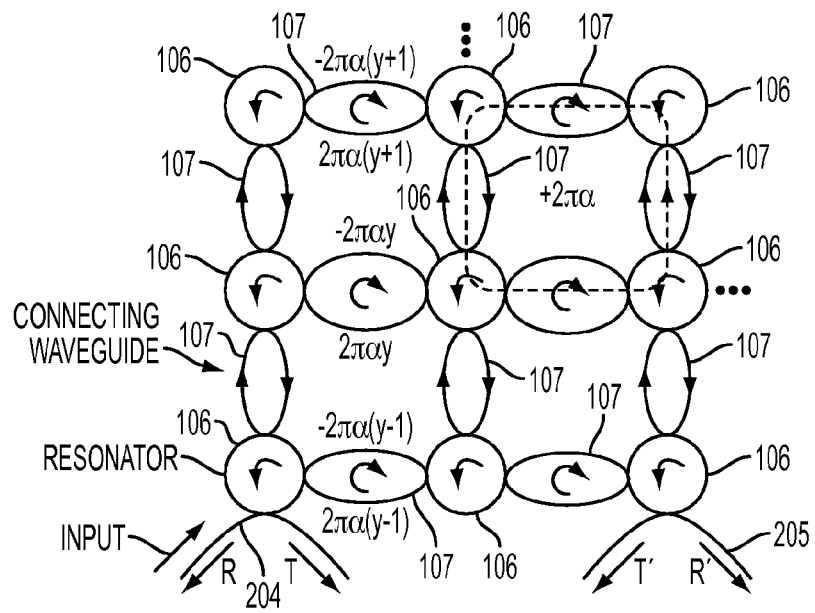
Figure 4C:
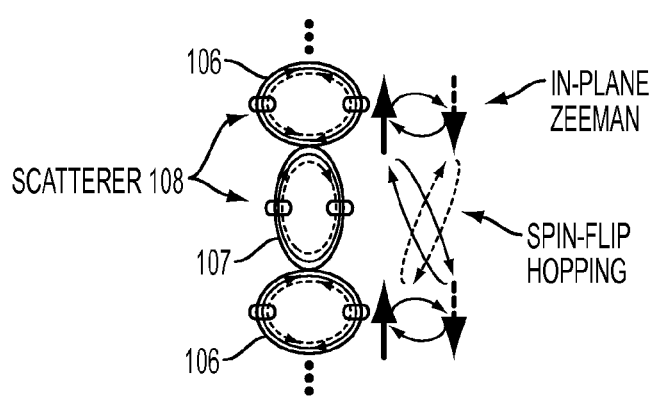

Turning now to FIGS. 4A-4C, embodiments of the present invention can include topological protected photonic devices implementing two-dimensional arrays of coupled resonator optical waveguides (CROWs) with linear optical devices, for instance. Photonic edge states of the two-dimensional array can carry light at the perimeter of the system, while being insensitive to disorder, and therefore can form a basis for robust photonic devices. As compared to one-dimensional CROW systems, embodiments of the present invention can be more resistant to scattering disorders and fabrication errors.

FIGS. 4A-4C, generally, are schematics of a photonic system (i.e., an array of resonators) with a synthetic magnetic field according to embodiments of the present invention.

A plurality of optical resonators 106 (e.g., optical microring resonators) can be provided that support degenerate clockwise and counter-clockwise modes, restricted to one pair per resonator. These modes can be considered as two components of a pseudo-spin, i.e., clockwise ($\sigma=-1$, or psuedo-spin down) and counter-clockwise ($\sigma=+1$, pseudo-spin up) circulation. Evanescently coupling of resonators, as in a one-dimensional CROW, can lead to a tight-binding model for photons and the corresponding photonic band structure. By coupling the degenerate clockwise and counter-clockwise modes in a two-dimensional arrangement, under appropriate conditions, the dynamics of such photonic system can be described by a Hamiltonian for charged bosons on a square lattice (tight-binding), but with the addition of a perpendicular, pseudo-spin-dependent effective magnetic field according to the following equation, where $\kappa$ is the coupling rate of optical modes and $\hat{a}^\dagger_{\sigma,x,y}$ is the photon creation operator at resonator at site (x,y) with different pseudo-spin components, $\sigma=\pm 1$:

$$H_0 = -\kappa \left( \sum_{\sigma,x,y} \hat{a}^\dagger_{\sigma x+1,y} \hat{a}_{\sigma x,y} e^{-i2\pi\alpha y\sigma} + \right.$$
$$\left. \hat{a}^\dagger_{\sigma x,y} \hat{a}_{\sigma x+1,y} e^{i2\pi\alpha y\sigma} + \hat{a}^\dagger_{\sigma x,y+1} \hat{a}_{\sigma x,y} + \hat{a}^\dagger_{\sigma x,y+1} \hat{a}_{\sigma x,y} \right)$$

Specifically, photons acquire a $2\pi\alpha\sigma$ phase when they go around a plaquette-equivalent to having $\alpha$ quanta of magnetic flux penetrating each plaquette. To derive the Hamiltonian description, consider two coupled resonators (FIG. 4A), focusing only on the counter-clockwise modes inside each resonator 106. The length of connecting waveguides 107 can be chosen such that photons destructively (constructively) interfere inside the waveguide loop (resonator), respectively, and therefore, they can be confined in the resonators 106 rather than waveguides 107. Moreover, the lengths of the upper and lower branches of the waveguide 107 can differ from each other, so when a photon "hops" from the left to the right resonator, it acquires a different phase than when it "hops" in the opposite direction. Thus, the lengths of the upper and lower branches differ from each other so that the phase difference is $4\pi\alpha$, where 'm' is an integer.

The boundary condition at the left resonator can be written as the following equation, where $\hat{E}_x$'s are waveguide electric field operators at the vicinity of the x-th resonator and $\hat{a}x$ is the resonator electric field operator, as shown in FIG. 4A.

$$\hat{E}_x^{out} = \hat{E}_x^{in} + \sqrt{2\kappa}\hat{a}_x$$

The resonator field equation is as follows, and similarly for the right resonator.

$$\partial_t \hat{a}_x = -\kappa \hat{a}_x - \sqrt{2\kappa} \hat{E}_x^{in}$$

Photons can propagate freely between the resonators. Accordingly, for the upper branch we have the following equation, and similarly for the lower branch:

$$E_{x+1}^{in} = i E_x^{out} \exp(-2\pi i \alpha)$$

By eliminating the waveguide fields, the left and right resonator fields dynamics will be given by the following equation, consistent with photon tunneling between resonators:

$$\partial_t \hat{a}_{x(x+1)} = i\kappa \exp(\pm 2\pi i\alpha)\hat{a}_{x+1(x)}$$

The corresponding Hamiltonian of the two resonators takes the form:

$$H_{two-res} = -\kappa \hat{a}^\dagger_{x+1} \hat{a}_x e^{-2\pi i\alpha} - \kappa \hat{a}^\dagger_x \hat{a}_{x+1} e^{2\pi i\alpha}$$

The above analysis for counter-clockwise modes (pseudo-spin up $\hat{a}_{\uparrow x,y}$) in the resonators shows that, in the absence of backscattering, they are decoupled from their time-reversed counterpart, i.e., the clockwise mode of the resonator (pseudo-spin down $\hat{a}_{\downarrow x,y}$). At the same time, the pseudo-spin down component will experience a magnetic field similar to the pseudo-spin up component, where only the sign of magnetic field is changed ($\alpha \rightarrow -\alpha$). By connecting resonators in a lattice structure, such as shown in FIG. 4B, and tuning the phase of the connecting waveguides according to embodiments of the present invention, the acquired phase can be arranged around each plaquette to be uniform and equal to $2\pi\alpha$. Note that in FIG. 4B, only the waveguide differences are shown. The phase can be tuned either by changing the length (and/or the index of refraction) of the connecting waveguides and/or by coupling ring resonators to the sides of the waveguides (e.g., similar to a Mach-Zehnder configuration). The implementation of a Landau-type gauge is shown in FIG. 4B where the corresponding Hamiltonian is the form of the first equation set forth above.

Generalized pseudo-spin-orbit interaction will now be discussed with respect to FIGS. 4A-4C.

Coupling between different pseudo-spin components can be controlled to exploit a wider class of Hamiltonians on a square lattice. In particular, semi-transparent scatterers inside the resonators 106 or the connecting waveguides 107 can be engineered to mix different pseudo-spin components with each other.

To illustrate this mixing, consider the addition of a pair of scatterers 108 in every vertical connecting waveguide of FIG. 4B, as shown in FIG. 4C. For simplicity, it can be assumed that the scattering is weak and does not introduce any loss. The strength of the scatterer can be characterized by a parameter $\epsilon$, where the transmission coefficient is near unity ($t_s \approx 1$) and the reflection coefficient is $r_s = i\epsilon/\sqrt{2}$. The corresponding Hamiltonian of a single vertical array of resonators can be represented by the following equation:

$$H_{flip} = -\kappa \sum_{x,y} \left( \hat{a}^\dagger_{\uparrow x,y+1} \; \hat{a}^\dagger_{\downarrow x,y+1} \right) \begin{pmatrix} 1 & \epsilon \\ \epsilon & 1 \end{pmatrix} \begin{pmatrix} \hat{a}_{\uparrow x,y} \\ \hat{a}_{\downarrow x,y} \end{pmatrix} + h.c..$$

Note that the diagonal terms are identical to the tight-biding terms of the first equation set forth above, and the off-diagonal terms represent hopping between two adjacent sites while undergoing a spin-flip, i.e., the scatterers couple clockwise to counter-clockwise photons (FIG. 4C). This spin-flip hopping is similar to the Rashba term in the context of spin-orbit interaction. Similarly, if we consider a pair of weak scatterers inside the resonators 106, then corresponding Hamiltonian takes the following form:

$$H_{mag} = -\kappa \sum_{x,y} \left( \hat{a}^\dagger_{\uparrow x,y+1} \; \hat{a}^\dagger_{\downarrow x,y+1} \right) \begin{pmatrix} 1 & 0 \\ 0 & 1 \end{pmatrix} \begin{pmatrix} \hat{a}_{\uparrow x,y} \\ \hat{a}_{\downarrow x,y} \end{pmatrix} +$$

$$h.c. - \frac{4\epsilon\kappa F}{\pi} \sum_{x,y} \left( \hat{a}^\dagger_{\uparrow x,y} \; \hat{a}^\dagger_{\downarrow x,y} \right) \begin{pmatrix} 0 & 1 \\ 1 & 0 \end{pmatrix} \begin{pmatrix} \hat{a}_{\uparrow x,y} \\ \hat{a}_{\downarrow x,y} \end{pmatrix}.$$

The first term is the usual tight-binding form and the second term represents the in-plane magnetic field which is enhanced by the finesse of the resonators (i.e., number of photon round trips $F \approx \pi/(1-r^2)$). If these vertical arrays replace the vertical arrays of FIG. 4B, then the overall Hamiltonian of the system encompasses both an in-plane Zeeman term (due to on-site scatters) and a hopping-spin flip term (similar to Rashba interaction).

Probing the photonic system of FIG. 4B now will be discussed in relation to the spectroscopy measurements shown in FIG. 5. As shown in diagrammatically in FIG. 4B, transmission T and reflection R of an input light field can be evaluated by coupling waveguides 204, 205 to the lattice edges. The magnetic states of the system (bulk states and edge states) will manifest in such transmission spectroscopy.

Consider the case of quantum spin Hall effect, where pseudo-spin-flip terms are absent. In this regime, there are two decoupled copies of regular quantum Hall states, one for each pseudo-spin components. Note that in the discussion to follow, the discussion of the analysis is from the standpoint that the analysis has been restricted to a single spin component and the spin index has been dropped. This choice can enable examination in detail methods for probing a system and determining its response to disorders.

Using formalism similar to the quantum scattering theory, the problem of scattering of light field in optical waveguides connected to our photonic system has been investigated and transmission and reflection coefficient under various conditions has been evaluated. The waveguides only couple to co-propagating modes in the resonators (counter-clockwise in FIG. 4B), and thus under the assumption, the reflection in the input channel and also transmission in the output channel is zero (i.e., R, T'=0 shown in FIG. 4B). The input-output waveguides 204, 205 can be coupled to two resonators in the systems denoted by |in> and |out>, respectively. The self-energy of these resonators can be written as the following, where the coupling strength is defined as v:

$$\sum = -i\frac{v}{2} |in\rangle\langle in| - i\frac{v}{2}|out\rangle\langle out|$$

Using Lippman-Schwinger equation, different reflection/transmission coefficients can be deduced. In particular, the reflection coefficient is given by the following equation, where co is the detuning from the resonators.

$$r'(\omega) = -iv \left\langle out \left| \frac{1}{\omega - H_0 - \Sigma} \right| in \right\rangle$$

Thus, appreciable reflection can be observed when the frequency of an incoming photon becomes resonant with the energy of a photonic state inside the system. Note that if the photonic system is a single resonator, equation immediately above reduces to the following equation:

$$r'(\omega) = \frac{v}{i\omega - v}$$

The energy spectrum of the $H_0$ for an infinite lattice is the Hofstadter butterfly. An $N_x \times N_y$ lattice with torus boundary condition (i.e., coupling top-bottom and left-right edges together) was considered to simulate the effect of an infinite lattice. According to Hofstadter spectrum, for rational magnetic fluxes ($\alpha = p/q$), each magnetic band has many states $(N_x N_y)/q$, which is reminiscent of Landau level degeneracy in the continuum. The result of the numerical solution is shown in FIG. 5, where the reflectivity ($R' = |r'(\omega)|^2$) was evaluated for different frequencies and magnetic field ($\alpha$), by the formalism described above. High reflectivity occurs when the lower waveguide light is coupled to the system and completely transferred to the reflection output channel (the second waveguide), similar to a channel drop filter. It can readily be seen that the energy spectrum of the uncoupled system (Hofstadter butterfly) can be obtained by measuring the system reflectivity. It is noted that in order to resolve different energy levels in the spectrum, the waveguide coupling (v) should be chosen to be sufficiently narrow, as set forth below, for instance:

($\leq 8\kappa/(N_x N_y)$)

Figure 5:
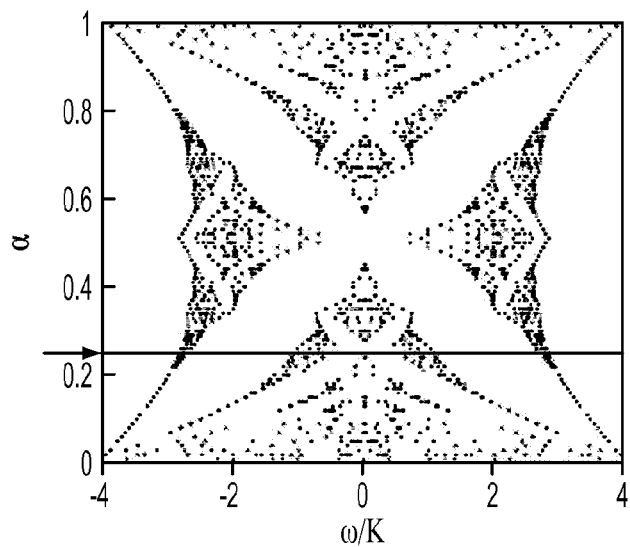
FIG. 5 is a graph showing a Hofstadter butterfly spectrum.

FIG. 5 is a graph showing a Hofstadter butterfly spectrum. Each point represents a reflectivity greater than 0.005 for a 10×10 lattice with torus boundary condition and the coupling v/κ=0.2. The horizontal line is the guide for eye to show the spectrum at the magnetic field of interest ($\alpha$) for FIGS. 6A-6D, 7A-C, and 8A-8B.

Figure 6:
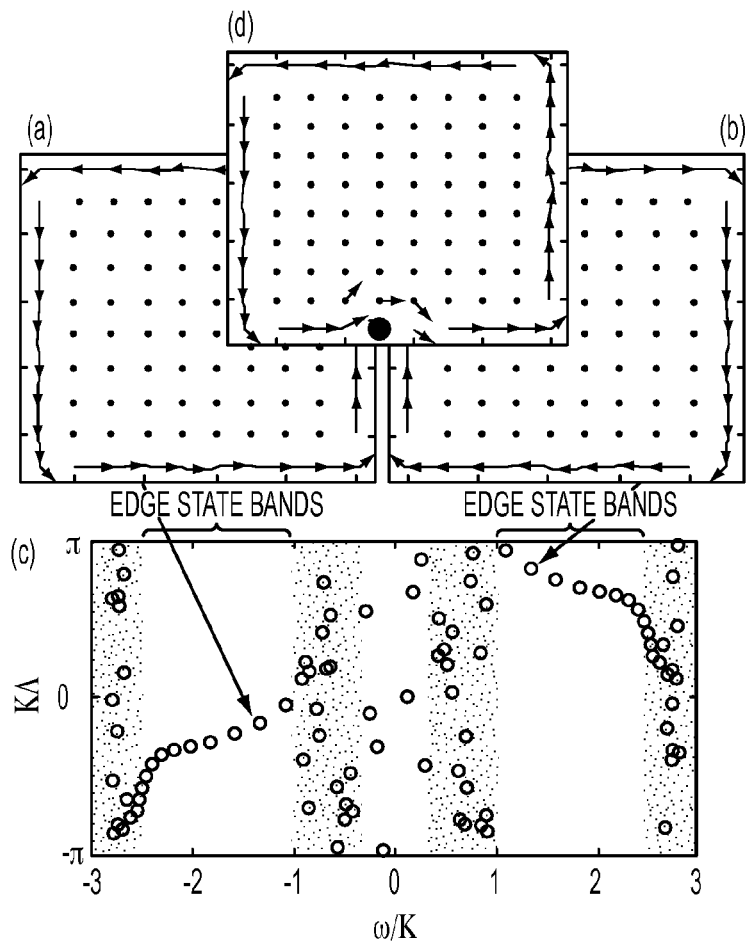
FIG. 6A-6D are diagrammatic representations showing information associated with photonic edge state bands and non-edge state bands according to embodiments of the present invention.

A discussion of photonic edge states will now ensue. In general, FIGS. 6A through 6D are directed to edge states and their dispersion. FIG. 6A shows light intensity for a forward-going edge state in the absence of disorder, and FIG. 6B shows its backward-going counterpart. FIG. 6C shows the dispersion relation, wherein a wave number is evaluated for each energy eigenstate at the lower edge, i.e., KΛ is the phase difference between two consecutive resonator at the edges. Note that magnetic bands state do not have a uniform phase difference along the edges and are shown in as the shaded vertical areas. The arrows show the states corresponding to the representations of FIGS. 6A and 6B. FIG. 6D shows the light intensity routing around the disorder (black dot, U/κ=20). In these plots, a 10×10 square lattice with α=¼ was considered.

In contrast to toroidal boundary conditions where only magnetic bands are present, in a finite square lattice, there exist states between magnetic bands which are known as "edge states." In particular, for certain bands, the field in resonators 106 located in the bulk (away from the edges) undergoes destructive interference, and therefore, the light intensity (i.e., the current probability of $\hat{a}_{x,y}$) is non-zero only at the edges. This is illustrated in FIG. 6A. For each edge state, there is a corresponding edge state with an opposite chirality (FIG. 6B). More specifically, the forward- and backward-propagating edge states take different paths, and consequently, they have different resonances at detunings, equal in magnitude and opposite in sign. For edge states, the phase difference between two consecutive resonators is uniform along the edges (i.e., well-defined momentum), and the system has a smooth dispersion (i.e. the phase difference is a smooth function of frequency), only in the edge state bands, as shown in FIG. 6C.

To illustrate the robustness of the system to disorder (i.e., its "fault-tolerantness"), consider that each resonator may be detuned from its neighbors. This can provide a model for "non-magnetic" disorder characterized by a random on-site potential at each site ($U_{x,y}\hat{a}^\dagger_{x,y}\hat{a}_{x,y}$). Such imperfections are a common problem in photonics and can prevent coupling large number of resonators.

Edge states are therefore immune to disorder. When disorder is located in the bulk, the edge state is not affected. However, when disorder is located on the edge, the edge state can route around the disorder, as shown in FIG. 6D for a single disordered site. Multiple disordered sites also may be accounted for. More precisely, scattering which can reverse the current is prevented since the backward going edge state has a different energy, thereby preventing elastic scattering.

As discussed earlier, array arrangements according to embodiments of the present invention can be implemented as a delay line or device, for instance, in computer circuitry, to delay information represented by the photons. For example, a delay line may be used to store photonic bits of data for later retrieval by a processor. Delay lines or devices according to embodiments of the present invention can be topologically protected and thus may be referred to as topological protected optical delay devices (TPODs).

Transport through edge states requires the photon to traverse the perimeter of the system, leading to a time delay. For illustrative purposes, FIGS. 7A-7C and 8A-8B compare the transport properties of a two-dimensional coupled resonator optical waveguide (used as a delay device) according to embodiments of the present invention that utilizes edge states (as shown in the left side of FIG. 7A (inset)) to a conventional one-dimensional CROW system (as shown in the right side of FIG. 7A (inset)).

Figure 7A:
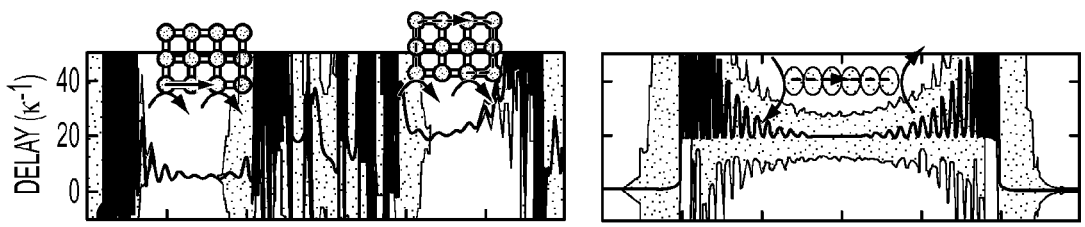
FIGS. 7A-7C and 8A-8B compare the transport properties of a two-dimensional coupled resonator optical waveguide according to embodiments of the present invention, as shown in the left side of these figures, to a conventional one-dimensional CROW system, as shown in the right side of these figures.
Figure 7B:
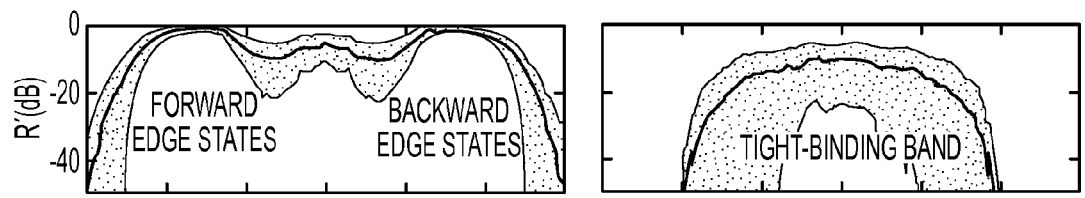
Figure 7C:
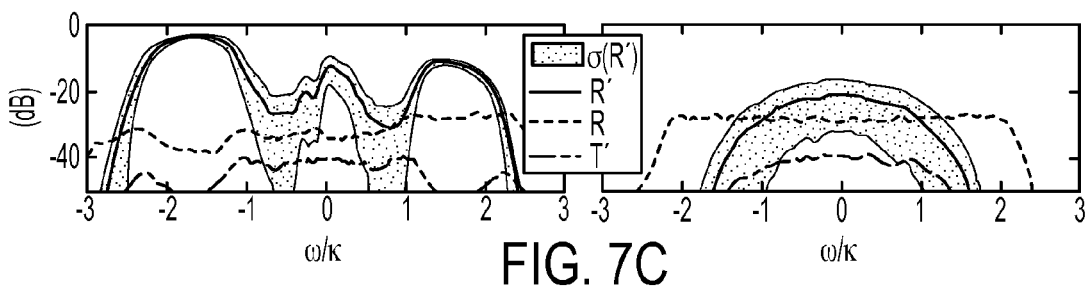

More specifically, FIGS. 7A-7C compare the performance of a two-dimensional coupled resonator optical waveguide according to embodiments of the present invention (left panels, 10×10 lattice) and the performance of a CROW system (right panels, array of 40) as delay lines. The darkest curves show the average time delay (output reflectivity) in FIGS. 7A and 7B, respectively, and the gray area highlights the standard deviations in the presence of non-magnetic disorder (a Gaussian disorder with $\sigma(U)/\kappa=0.4$ for 500 realizations). While the transport is quite noisy in the magnetic bands and CROW (tight-binding band), the edge state bands exhibit noiseless transport with delays comparable to CROW. Depending on the input frequency, different edge states can participate in the transport, which leads to shorter or longer delays, as shown in the insets.

FIG. 7C shows a comparison in magnetic disorder between the two systems. Beside the non-magnetic disorder, in order to estimate the effect of magnetic disorder and loss, a Gaussian distribution of magnetic noise (mode coupling) with a width $\epsilon F=0.1$ and a random phase ($[0, 2\pi)$) and an intrinsic loss ($\kappa_{in}=0.02\kappa$), is assigned to each resonator. The transport properties are shown as more degraded for CROW than edge state bands according to embodiments of the present invention. While the counter-clockwise modes of the resonators are excited through an input field, the onsite scatterers backscatter photons in the clockwise modes. These modes lead out into R and T' channels which are non-zero in these plots. The coupling between input-output waveguides and the system can be chosen to optimize the transport (for edge states $\nu=6\kappa$ and for CROW $\nu=2\kappa$). In the two-dimensional coupled resonator optical waveguide according to embodiments of the present invention, the input and output waveguides are coupled to $(x=2, y=1)$ and $(x=N_x-1, y=1)$ resonators, respectively.

Figure 8A:
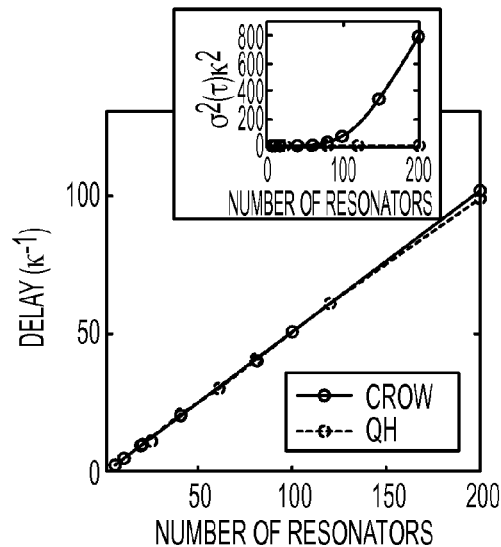
Figure 8B:
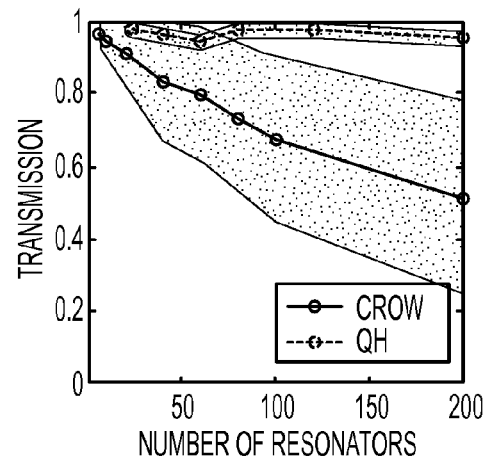

FIGS. 8A and 8B specifically show a comparison of localization in the one-dimensional CROW system versus non-localization of the two-dimensional coupled resonator optical waveguide according to embodiments of the present invention. FIG. 8A compares time delay and FIG. 8B compares transmission (R'). For one-dimensional CROW (versus the present two-dimensional array), the transport properties are evaluated at the center frequency $\omega=0$ ($\omega=1.5\kappa$), where the group velocity dispersion is minimum, respectively. A Gaussian disorder is assumed with $\sigma(U)/\kappa=0.14$ and the transmission is averaged over an ensemble of 1000 realizations. By increasing the system length/perimeter (x-axis), the transmission for one-dimensional CROW decreases and the noise (standard deviation in gray) increases, while both the transmission and the noise in the two-dimensional coupled resonator optical waveguide example according to embodiments of the present invention remains constant. The inset in FIG. 8A shows the standard deviation of the time delay in both systems. In order to highlight the effect of localization, the loss is ignored in these plots.

In the two-dimensional coupled resonator optical waveguide according to embodiments of the present invention, there is a robust transfer band provided by edge states which carry photons from the input waveguide to the output waveguide. See the left side of FIG. 7A.

Both systems are considered first without disorder to find their operational bandwidth and delay time in transport.

In both cases, the operational bandwidth is given by smooth, linear part of the dispersion relation. In the two-dimensional coupled resonator optical waveguide according to embodiments of the present invention, the edge state band (FIG. 6C), is located between two Hofstadter bands (FIG. 5), while in the CROW configuration, the operational bandwidth is in the middle of the tight-binding dispersion to avoid the group velocity dispersion. Moreover, in both systems, the delay time is proportional to the number of resonators involved in the transport ($\tau \approx (\kappa/2)N$), as shown in FIG. 8A. In the two-dimensional coupled resonator optical waveguide according to embodiments of the present invention, the transport can be either performed along the long or short edge of the system, depending on the input frequency, as shown schematically in the examples of the left side of FIG. 7A (inset). In both systems in the absence of disorder, the bandwidth-delay product increases by the length/perimeter of the system.

However, in the presence of disorder, CROW and edge state behave differently as the system size increases. In particular, in one-dimensional systems (such as CROW), the disorder can lead to localization and therefore, the transmission may be impeded. More specifically, one finds a localization length $l \approx 10\kappa^2/\text{var}(U)$ where var(U) is the variance of the disorder; when $N_x>l$, all states are localized, while for $N_x<l$ the transmission is drastically perturbed and "ripples" appear in the transmission spectrum and the delay time spectrum.

Decreasing the resonator quality factor effectively increases the localization length and postpones the localization effects; nevertheless, the noise in the time delay increases with the number of resonators. Physically the forward- and backward-going states have the same energy and spatially overlap, and therefore, they can scatter to each other. In contrast, in two-dimensional coupled resonator optical waveguides according to embodiments of the present invention, the forward- and backward-going edge states have different energies and are topologically protected against disorder.

A numerical study of the effect of disorder confirms that the edge states in the two-dimensional coupled resonator optical waveguide according to embodiments of the present invention provide a robust transport. A random frequency mismatch can be assigned to each resonator and an average over many "frozen" disorder realizations can be taken. By studying the transmission at the "sweet" frequency ($\omega=0$ for one-dimensional CROW and the middle of edge state band ($\omega=1.5\kappa$) for the two-dimensional coupled resonator optical waveguide according to embodiments of the present invention), it can be observed that by increasing the system length/perimeter, the transmission in CROW decreases while the transmission through edge states is unaffected, as shown in FIG. 8B. Similarly the delay changes from system to system in the one-dimensional CROW; single disorder realization exhibits ripples in the transmission and delay time spectrum. To characterize this behavior, the standard deviation for each frequency can be evaluated, showing that while the "time delay ripples" increases in one-dimensional CROW, the example of the two-dimensional coupled resonator optical waveguide according to embodiments of the present invention shows almost a complete absence of such ripples.

Both the two-dimensional coupled resonator optical waveguide according to embodiments of the present invention and the one-dimensional CROW can be compared for a fixed system size and to study the transport spectrum and evaluate the effect of disorder on the operational bandwidth (FIGS. 7A-7C). It was observed that while both magnetic band states and CROW depend sensitively on the disorder (position/strength), from one realization to another, the edge states can be insensitive to the specific parameters, as shown in the standard deviation of the reflectivity and delay time in FIGS. 7A and 7B.

Note that as time-reversal symmetry is not broken in the two-dimensional coupled resonator optical waveguide according to embodiments of the present invention, such edge states cannot be used as a one-way waveguide. More precisely, when a light field is input in the backward direction into the two-dimensional coupled resonator optical waveguide according to embodiments of the present invention (by swapping the input and output channel), the waveguides couple to the opposite rotating field in the resonators (opposite pseudo-spin) and experience a magnetic field with an opposite sign. Therefore, the system is reciprocal and the transport properties of the forward and backward feed are identical to each other.

The effect of loss in the resonators and other imperfections have also been investigated. Loss can be represented by a non-hermitian term in the Hamiltonian: $-i\kappa_{in}\hat{a}^\dagger_x\hat{a}_x$ where $\kappa_{in}$ characterizes propagation, bending and coupling losses. The photonic loss attenuates the reflection in the edge state transfer band due to the propagation around perimeter (FIG. 7C). The effect of loss is similar in both one- and two-dimensional cases, and its magnitude is proportional to the number of resonators traversed by light. Incidentally, two-dimensional coupled resonator optical waveguides according to embodiments of the present invention may be implemented in silicon-on-insulator (SOD technology, for instance.

Other types of imperfection such as surface roughness can cause undesired backscattering which mixes pseudo-spin up and down, acting as "magnetic disorder." These imperfections can be modeled by a magnetic disorder Hamiltonian. The backscattering effect manifests in the reduction of signal in R', T channels and some leakage in R, T' channels. FIG. 7C shows these transport coefficients. It can be observed that although the transport properties of one-dimensional CROW and magnetic bands states are affected by such magnetic disorder, edge state transport, as implemented according to embodiments of the present invention, remains robust (i.e., not affected or not significantly affected), due to the suppression of backscattering events. In particular, the scattering of a forward-going spin-up into forward (backward)-going spin-down is partially inhibited due to energy mismatch.

Delay lines implementing two-dimensional coupled resonator optical waveguide arrays according to embodiments of the present invention may be static or dynamic delay lines. That is, the delay of a delay line may be set or it may be variable. For instance, in embodiments, a switch or switches may couple or decouple multiple two-dimensional coupled resonator optical waveguide arrays together in series, thereby increasing or decreasing the delay of the overall line depending upon the state of the switch or switches and the number of arrays in the series.

Optionally or alternatively, a number of individual two-dimensional coupled resonator optical waveguides arrays of different size and consequently different delays can be connected to a same input waveguide, for instance side-coupled to a corner resonator in each of the arrays, such that light signals at a first frequency will enter only one of the arrays and be delayed by the delay of that array, and such that light signals at a second frequency will enter only another of the arrays and be delayed by the delay associated with that array, and so on and so forth depending upon the number of individual arrays.

Figure 12:
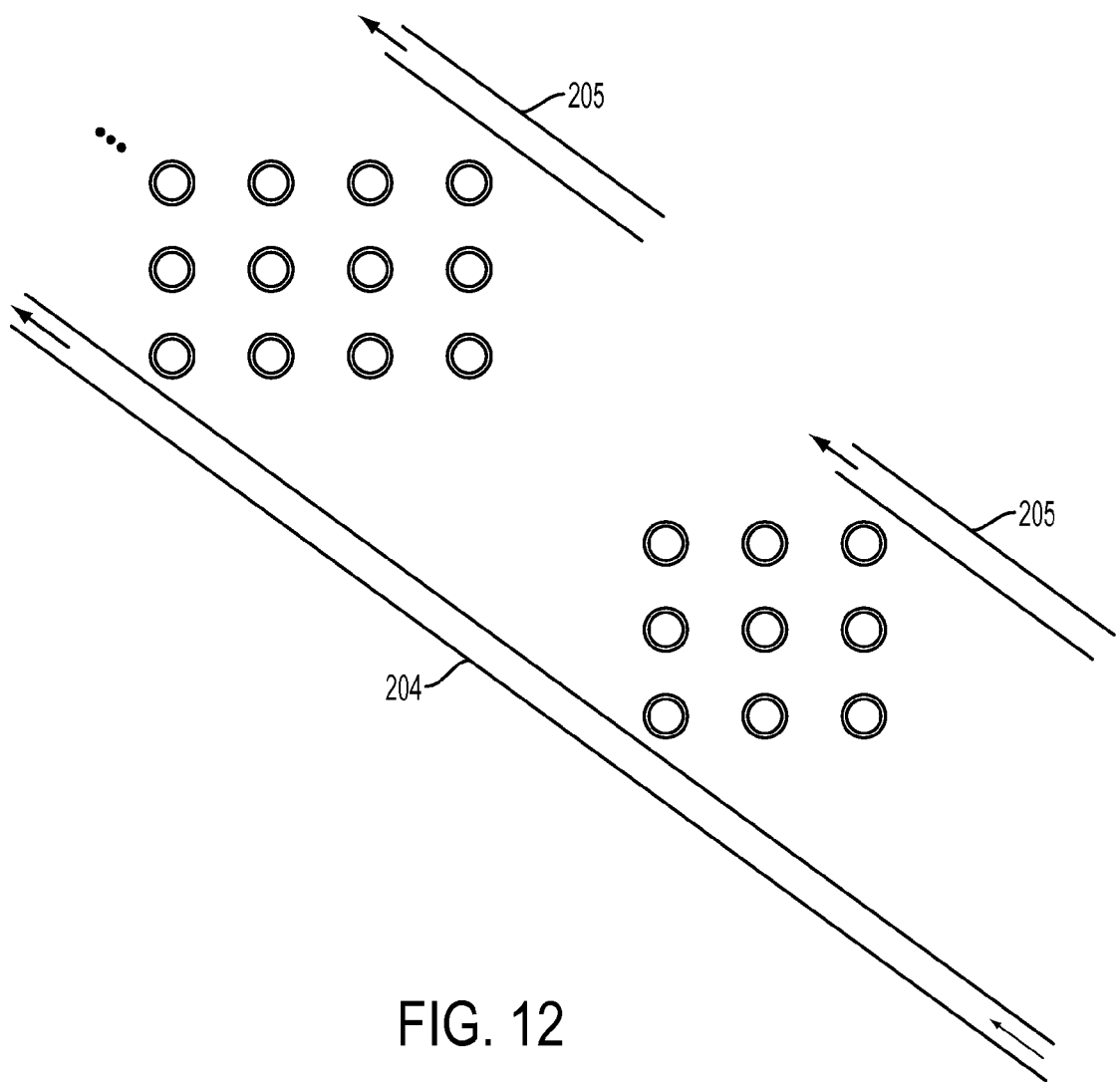
FIG. 12 is a block diagram of a delay system according to embodiments of the present invention.

FIG. 12 shows an example of such a variable delay configuration. Light signals can travel along waveguide 204 and be evanescently coupled to one of the first shown array or the second shown array it encounters, depending upon the configuration of the resonators of the respective arrays and the frequency of the light signal. Light signals can be output from the respective arrays via waveguides 205, which may be a same waveguide for some or all arrays or separate output waveguides for each array.

As another example of variable delay lines or devices according to embodiments of the present invention, variable delay may be provided by changing the index of refraction for the array using a laser, for instance. Additional examples include providing a PIN junction and applying an electric field; providing a heating pad, for instance, to the entire array (or optionally the system), such that there is no temperature gradient; providing a metal-oxide-semiconductor capacitor structure; and/or a mechanical stress or strain.

Figure 9:
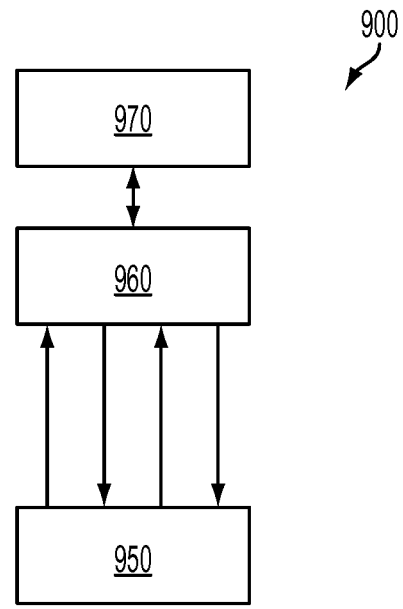
FIG. 9 is a block diagram of a system according to embodiments of the present invention.

FIG. 9 is a block diagram of a system 900 according to embodiments of the present invention.

The block diagram shown in FIG. 9 is a basic block diagram of system 900, which can represent any of the systems or devices shown and/or described herein, including computer systems implementing delay lines or devices as shown and described herein, as well as sensing systems (e.g., chemical and bio sensors) and photon pair generation systems as shown and described herein.

System 900 can include one or more two-dimensional coupled resonator optical waveguides arrays 950 as set forth herein, which can be coupled to a light transceiver 960 via light transmission means 955. Light transceiver 960 can be any suitable light source, including a laser (e.g., a tunable laser) or a light-emitting diode (LED) or diodes. Light transmission means 955 can be any suitable transmission means to transport light signals from light transceiver 960, such as one or more waveguides (e.g., slot waveguides or normal waveguides, i.e., rectangular cross section).

Additionally, light signals can be output from the one or more arrays 950 and provided to light transceiver 960. Alternatively, the light transceiver 960 may be separate transmitting and receiving/sensing units. A processor 970 can be coupled to light transceiver 960 and can send instructions to control the light signal output from the light transceiver 960 and/or to receive data from light transceiver (or separate receiver/sensor).

Figure 10:
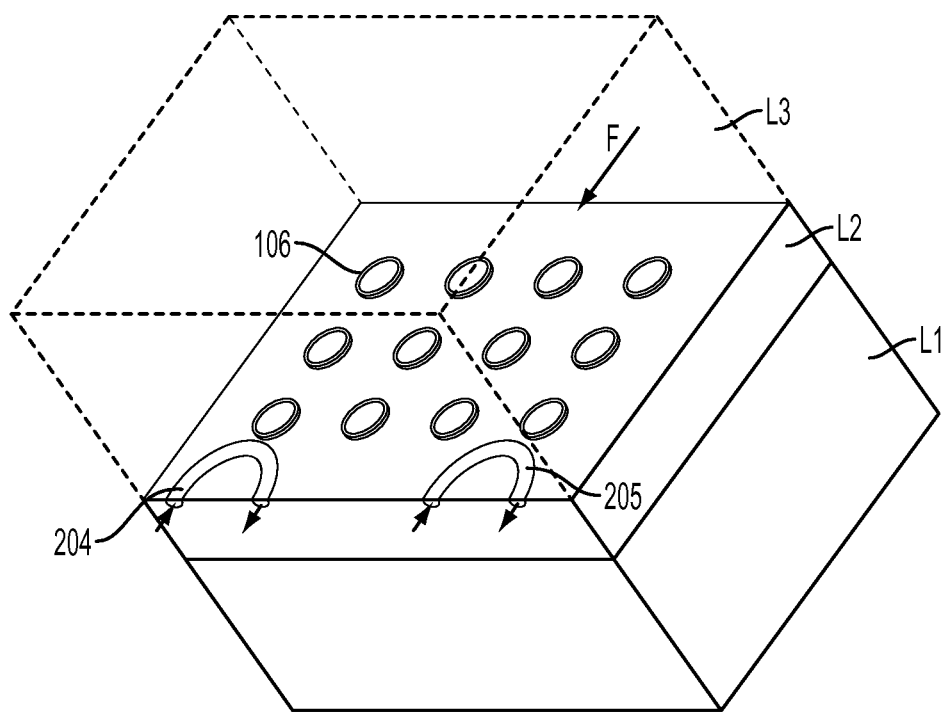
FIG. 10 is a diagram of a portion of a sensor according to embodiments of the present invention.

FIG. 10 is a diagram of a portion of an optical-based sensor according to embodiments of the present invention. Optical-based sensors according to embodiments of the present invention can be used for medical diagnostics, food quality control, drug development, and environmental monitoring, for example.

Optical sensors according to embodiments of the present invention can be for biosensing and for analytical chemistry purposes to perform label-free, fluorescence-labeled, and/or Raman based detection of molecule-molecule interactions (e.g., biomolecule-biomolecule interactions), for instance. Further, sensors according to embodiments of the present invention can perform bulk mass (or refractive index (RI)) detection, in which analytes are present homogeneously in buffer, and surface mass (or RI) detection, in which analytes are present at the solid-liquid interface. Single-molecule detection and multi-molecule detection can be performed.

Generally, a waveguide-based array of optical resonators can be used as a sensor with or without application of a surface chemistry to a top surface of the cladding L2 covering waveguide. In the case of surface chemistry application, this can result in a thin layer (e.g., a biolayer) on top of the waveguide cladding that contains immobilized receptor molecules that are specific to the analyte, i.e., the molecule that one wants to detect. Incidentally, the surface modification may also prevent non-specific protein absorption.

A solution L3 containing the analyte may be applied to the upper layer of the cladding or biolayer via an enclosed chamber or a channel (e.g., a micro- or nano-channel) as part of a circuit, represented by flow F in FIG. 10, and a molecule-molecule interaction can take place at the solid-aqueous interface, for instance. Light can be input to the two-dimensional coupled optical resonator array according to embodiments of the present invention via waveguide 204, for instance, generated by a tunable laser. The evanescent field of the guided light in the waveguide can extend into the surrounding medium (e.g., the solution L3) and interact with the interacted molecules near the top surface of the cladding L2 (and optionally the biolayer). A change in the refractive index near the surface when target analytes are captured can cause modifications in the optical signal (such as phase or spectral shift) at the output, which can be output by waveguide 205 and sensed by a sensor in order for a processor, for instance, to determine characteristics of the molecule-molecule interactions. Thus, by directly or indirectly monitoring the spectral shift in whispering gallery modes (WGMs), both quantitative and kinetic information can be obtained about molecule binding at or near the surface. For example, direct detection of biomolecules can enable the monitoring of the dynamics of molecular reactions, quantitative concentration measurements, and/or determination of affinity constants.

In embodiments of the present invention, detection or sensing can be automatic and/or multiplexed with other two-dimensional coupled optical resonator arrays according to embodiments of the present invention. For instance, a plurality of two-dimensional arrays as set forth herein may be cascaded on a common input/output pair and used to simultaneously detect different biological species through wavelength division multiplexing (wdm). Further, each of the arrays may be individually addressable. Two-dimensional arrays according to embodiments of the present invention can also be implemented with capillary-based optofluidic ring resonators (OFRR).

Figure 11:
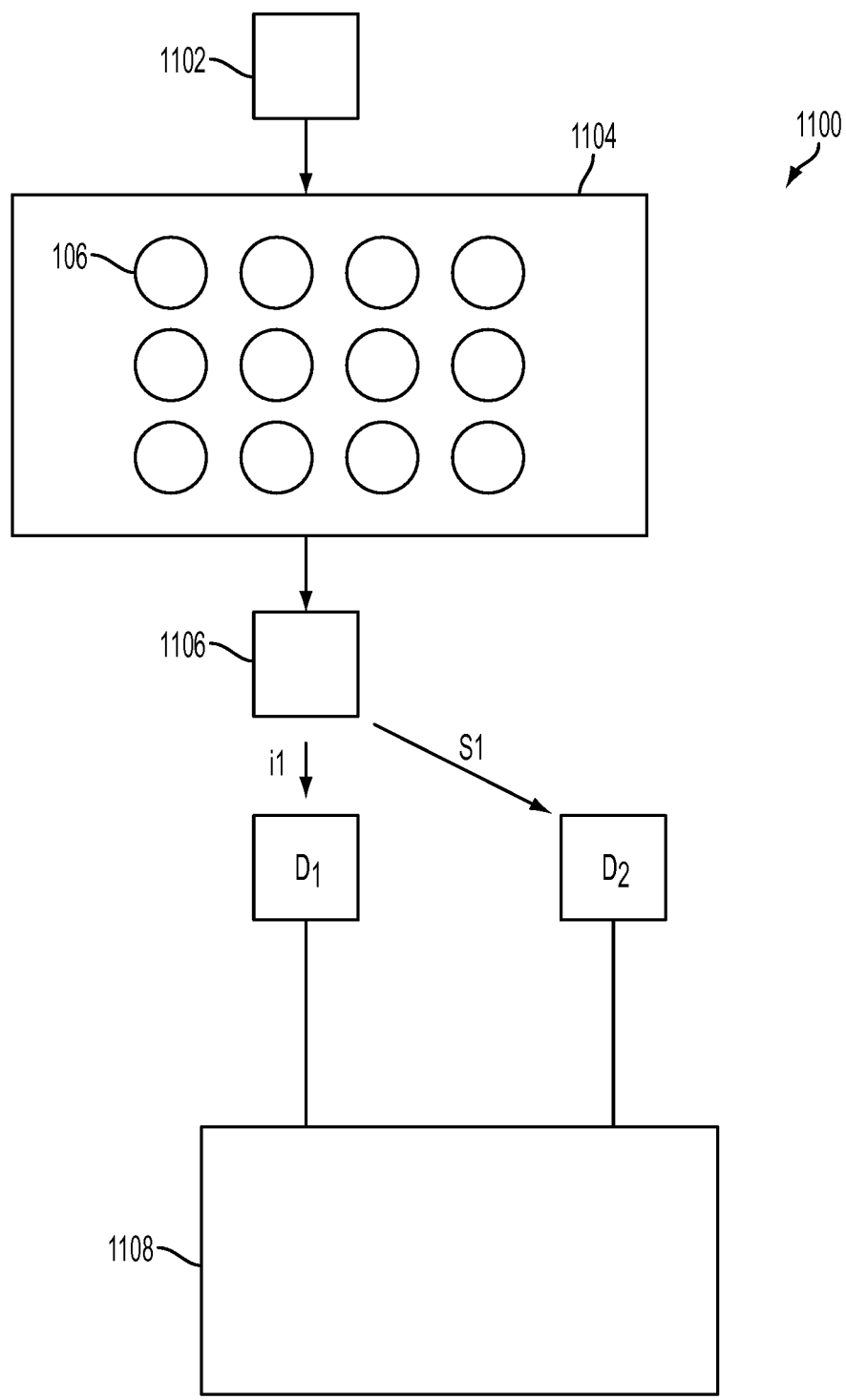
FIG. 11 is a block diagram of a system or device for generating photon pairs according to embodiments of the present invention.

FIG. 11 is a basic block diagram of a system or device 1100 for generating photon pairs according to embodiments of the present invention.

Generally speaking, two-dimensional coupled resonator optical waveguides 1104 according to embodiments of the present invention can be implemented in a light signal path, wherein the light signal (e.g., a pulsed light signal) can be generated by a light source 1102, such as a tunable laser. Additional optical elements may be between the light source 1102 and two-dimensional coupled resonator optical waveguides 1104, but are omitted for simplicity. The output of the two-dimensional coupled resonator optical waveguides 1104 may be coupled to a photon pair generation source 1106 which can generate or otherwise emit a correlated photon pair idler i1 and signal s1. Additional optical elements may be provided between the two-dimensional coupled resonator optical waveguides 1104 and the photon pair generation source 1106. The photon pairs can be detected by respective detectors D1, D2 and their respective signals sent to processor 1108, for instance.

The photon pair generation system or device 1100 may be implemented in a quantum communication system, such as a quantum key distribution (QKD) system, a quantum computer (QC) system, or a quantum repeater (QR) system.

In addition, embodiments of the two-dimensional coupled resonator optical waveguides according to embodiments of the present invention can enable approaches for exploration of various fundamental quantum Hall phenomena, including investigation of quantum Hall physics by simulating different types of Hamiltonians at room temperature, as well as forming various system topologies (tori with different genera, cylinders, Möbius strip or band) by connecting two two-dimensional coupled resonator optical waveguides in different planes to each other and thereby manipulating such states for topological quantum computation.

Figure 13:
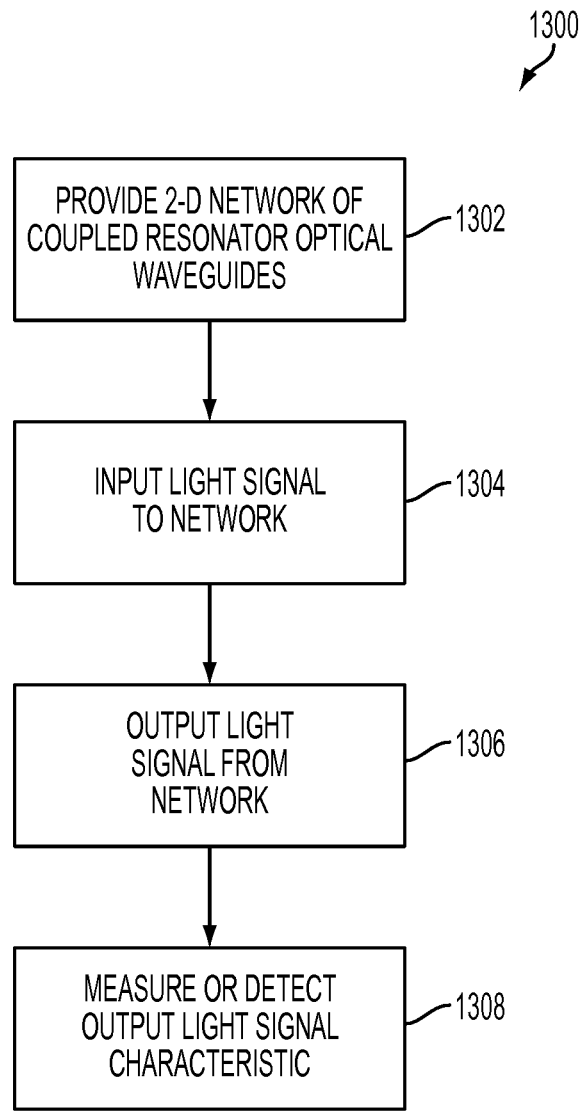
FIG. 13 is a block diagram of a method according to embodiments of the present invention.

FIG. 13 is a block diagram of a method 1300 according to embodiments of the present invention.

Generally speaking, method 1300 can include traversal of a photon or light signal in an edge state path of a topologically protected two-dimensional coupled resonator optical waveguide according to embodiments of the present invention in accordance with an effective magnetic field associated with the edge states.

At 1302 a two-dimensional network of coupled resonator optical waveguides can be provided as disclosed and shown herein. The two-dimensional network of coupled resonator optical waveguides may be fabricated in silicon in insulator (SOI) technology, for instance, using optical lithography techniques, such as deep ultraviolet lithography or extreme ultraviolet lithography (EUVL).

At 1304, light signals can be received at an access portion of a two-dimensional network of coupled resonator optical waveguide, via a waveguide, for instance, and at 1306 the light signals can be output from the two-dimensional network of coupled resonator optical waveguide at an egress portion.

Outputting of the photon is after the photon has traversed a path through the network based on a magnetic field. In the case where the light signals encounter a disorder (e.g., at the perimeter), the light signals can be routed around the disorder. In the case where the disorder is not in the path of the light signals, the light signals may not be rerouted. At 1308, a characteristic of the output light signal may be sensed or detected, such as a delay time of the light, an amount of degradation, a phase change, etc.

Having now described embodiments of the disclosed subject matter, it should be apparent to those skilled in the art that the foregoing is merely illustrative and not limiting, having been presented by way of example only. Numerous modifications and other embodiments (e.g., combinations, rearrangements, etc.) are within the scope of one of ordinary skill in the art and are contemplated as falling within the scope of the disclosed subject matter and any equivalents thereto. It can be appreciated that variations to the disclosed subject matter would be readily apparent to those skilled in the art, and the disclosed subject matter is intended to include those alternatives. Further, since numerous modifications will readily occur to those skilled in the art, it is not necessarily desired to limit the disclosed subject matter to the exact construction and operation illustrated and described, and accordingly, all suitable modifications and equivalents may be resorted to, falling within the scope of the disclosed subject matter.

The invention claimed is:

1. A topologically protected device comprising:
   a two-dimensional array of coupled micro-resonator waveguides having four or more micro-resonators, said two-dimensional array being of any geometry;
   an input waveguide arranged adjacent to a first micro-resonator of the four or more micro-resonators such that photons in said input waveguide are coupled to only said first micro-resonator and not any other micro-resonators of said four or more micro-resonators; and
   an output waveguide arranged adjacent to a second micro-resonator of said four or more micro-resonators, different from said first micro-resonator, such that photons are coupled from only said second micro-resonator to said output waveguide and not from any other micro-resonators of said four or more micro-resonators,
   wherein said two-dimensional array is arranged so as to be operative to provide topological protection against any disorders in said two-dimensional array,
   the topological protection including providing an alternative pathway for photons traveling along a portion of the perimeter of said two-dimensional array based on photonic edge states thereof such that the traveling photons bypass any disorder in a photon path from said first micro-resonator to said second micro-resonator and such that the traveling photons coupled to the output waveguide from the second micro-resonator are unaffected by any disorder in the two-dimensional array.

2. The topologically protected device according to claim 1, wherein the portion of the perimeter for the photon path from said first micro-resonator to said second micro-resonator is less than the entire perimeter of said two-dimensional array.

3. The topologically protected device according to claim 1, wherein edge state transmission along the portion of the perimeter for said two-dimensional array is based on the operational bandwidth of said four or more micro-resonators in said two-dimensional array.

4. The topologically protected device according to claim 1, wherein the light signals traveling along the portion of the perimeter of said two-dimensional array based on photonic edge states thereof do so based on a magnetic field equivalent.

5. The topologically protected device according to claim 4, wherein the magnetic field equivalent is a pseudo magnetic field.

6. The topologically protected device according to claim 4, wherein the magnetic field equivalent is based on phase tuning of waveguides connecting said four or more micro-resonators to each other, said phase tuning being based on the respective lengths of the connecting waveguides and/or a change in an index of refraction for the connecting waveguides.

7. The topologically protected device according to claim 1, wherein the delay line is a variable delay line, the variability of the delay being based on at least one of a switch or switches coupling or decoupling said two-dimensional array in series with one or more other one- or two-dimensional arrays, changing the index of refraction for said two-dimensional array, a PIN junction, a heating element providing a uniform heat distribution, and a metal-oxide-semiconductor capacitor structure.

8. The topologically protected device according to claim 1, wherein said four or more micro-resonators of said two-dimensional array are arranged as a square, a rectangle, a disk, an oval, a diamond, a triangle, lattice structure or any other shape or structure having the same topology of these arrangements.

9. The topologically protected device according to claim 1, wherein the delay line is provided in an optical computation and communication system.

10. A fault-tolerant system comprising:
    a two-dimensional waveguide array of coupled resonators, said two-dimensional array being of any geometry;
    one or more input waveguides operatively coupled to said two-dimensional waveguide array, photons being input to the two-dimensional waveguide array via the one or more input waveguides; and
    one or more output waveguides operatively coupled to said two-dimensional waveguide array, photons being output from the two-dimensional waveguide array via the one or more output waveguides,
    wherein the resonators are arranged and coupled to each other such that photons traveling through the two-dimensional waveguide array and output from the two-dimensional waveguide array via the one or more output waveguides are unaffected by any faults within the two-dimensional waveguide array, and
    said faults include faults caused by one of a defect in a corresponding wafer, a defect due to fabrication errors, and a defect due to degradation over time.

11. The fault-tolerant system according to claim 10, further comprising:
    a light transmitter to transmit light signals to said two-dimensional waveguide array via said one or more input waveguides;
    a light receiver to receive light signals from said two-dimensional waveguide array via said one or more output waveguides; and
    a processor to receive and process data from said light receiver based on the received light signals.

12. The fault-tolerant system according to claim 10, wherein the system is a delay system in a computer system or a communication system.

13. The fault-tolerant system according to claim 10, wherein the system is a sensing system.

14. The fault-tolerant system according to claim 10, wherein said two-dimensional waveguide array of coupled resonators are operatively multiplexed with a plurality of other said two-dimensional waveguide arrays of coupled resonators.

15. The fault-tolerant system according to claim 10, wherein the fault-tolerant system is a system for generating photons pairs.

16. A method for routing photons of electromagnetic radiation, the method comprising:
   receiving a photon at an access portion of a topologically protected two-dimensional lattice of coupled resonators; and
   outputting the photon from the topologically protected two-dimensional lattice of coupled resonators at an egress portion thereof,
   wherein said outputting the photon is after the photon has traversed an edge state path of the topologically protected two-dimensional lattice of coupled resonators in accordance with the edge state, and
   photons output from the topologically protected two-dimensional lattice of coupled resonators are unaffected by any faults within the topologically protected two-dimensional lattice of coupled resonators.

17. The method according to claim 16, further comprising:
   applying a solution to a surface associated with the topologically protected two-dimensional lattice of coupled resonators; and
   sensing a molecule-molecule interaction at the interface of the surface and the solution.

18. The method according to claim 16, further comprising outputting a photon pair based on said outputting the photon from the topologically protected two-dimensional lattice of coupled resonators.

19. The method according to claim 16, further comprising dynamically varying the time it takes the photon to be outputted by said outputting from the time of said receiving.

20. The topologically protected device of claim 1, wherein the traveling photons coupled to the output waveguide are unaffected with respect to wavelength, phase, delay, power, and noise despite any disorder in the two-dimensional array.

21. The topologically protected device of claim 1, further comprising a plurality of connecting waveguides, each connecting waveguide coupling a corresponding one of the micro-resonators to an adjacent micro-resonator, at least some of the connecting waveguides being constructed different from others of the connecting waveguides so as to introduce a predefined phase shift to a traveling photon.

22. The topologically protected device of claim 1, wherein:
   the two-dimensional array includes a first set of the micro-resonators arranged on a perimeter of the array and a second set of the micro-resonators arranged internal to the perimeter and surrounded by the first set of micro-resonators, and
   the two-dimensional array has an edge state band for photons having a first wavelength such that photons having the first wavelength travel along a perimeter path defined by the first set of micro-resonators and undergo destructive interference within the second set of micro-resonators unless a disorder is in said perimeter path.

* * * * *